United States Patent [19]

Ikeda et al.

[11] Patent Number: 5,734,050
[45] Date of Patent: Mar. 31, 1998

[54] PROCESS FOR PRODUCING DIOXAZINE COMPOUNDS, COLORED MATERIALS THEREWITH AND DIOXAZINE COMPOUNDS HAVING A PLATE-LIKE CRYSTAL FORM

[75] Inventors: Masaaki Ikeda; Junko Yoshioka, both of Yono; Masao Onishi, Saitama-ken, all of Japan

[73] Assignee: Nippon Kayaku Kabushiki Kaisha, Tokyo, Japan

[21] Appl. No.: 450,192

[22] Filed: May 25, 1995

[30] Foreign Application Priority Data

May 30, 1994 [JP] Japan .................................. 6-137882

[51] Int. Cl.$^6$ .................................................. C07D 498/22
[52] U.S. Cl. .................................................. 544/74
[58] Field of Search .................................................. 544/74

[56] References Cited

U.S. PATENT DOCUMENTS

| | | | |
|---|---|---|---|
| 4,253,839 | 3/1981 | Spietschka et al. | 88/565 |
| 4,526,963 | 7/1985 | Deur | 544/74 |
| 5,275,653 | 1/1994 | Dietz et al. | 106/498 |
| 5,318,627 | 6/1994 | Dietz et al. | 106/498 |

FOREIGN PATENT DOCUMENTS

| | | |
|---|---|---|
| 0234870 | 2/1987 | European Pat. Off. . |
| 0504922 | 9/1992 | European Pat. Off. . |
| 0504923 | 9/1992 | European Pat. Off. . |
| 0606632 | 7/1994 | European Pat. Off. . |
| 3239321 | 5/1983 | Germany . |
| 54-56630 | 5/1979 | Japan . |
| 58-120673 | 7/1983 | Japan . |
| 60-11986 | 3/1985 | Japan . |
| 2102272 | 4/1990 | Japan . |
| 2102273 | 4/1990 | Japan . |

OTHER PUBLICATIONS

Journal of Heterocyclic Chemistry., vol. 27, 1990, pp. 1575–1579.
Kozawa et al. "Carbazoledioxanes . . . " Jul. 1990.

Copy of the European Search Report in English dated Aug 25, 1995.

PB Report 65657 "German Dyestuffs and Dyestuffs Intermediates" (1946), Sep.

*Primary Examiner*—Mukund J. Shah
*Assistant Examiner*—Bruck Kifle
*Attorney, Agent, or Firm*—Nields, Lemack & Dingman

[57] ABSTRACT

The present invention relates to a process for producing a dioxazine compound represented by the formula (1) which comprises carrying out a ring closure reaction of a compound represented by the formula (2) in the presence of a dioxazine derivative of the formula (3):

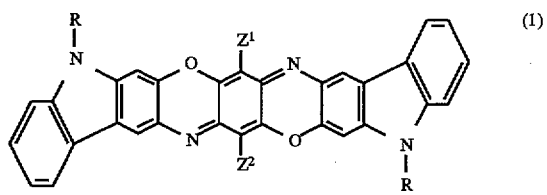

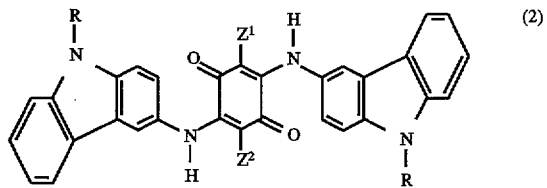

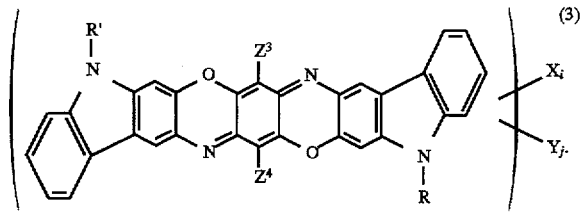

11 Claims, 1 Drawing Sheet

PROCESS FOR PRODUCING DIOXAZINE COMPOUNDS, COLORED MATERIALS THEREWITH AND DIOXAZINE COMPOUNDS HAVING A PLATE-LIKE CRYSTAL FORM

FIELD OF THE INVENTION

The present invention relates to a process for producing dioxazine compounds useful as pigment, materials colored with said compounds and dioxazine compounds having a plate-like crystal form.

BACKGROUND OF THE INVENTION

For preparing a compound of the formula (1) shown below, a process is known in which 3-amino-9-alkylcarbazole of the formula (5) shown below and chloranil are condensed in an inert solvent in the presence of an acid coupling agent to obtain a compound of the formula (2) shown below and this compound is subjected to ring closure using a ring-closing agent (PB Report 65,657, Japanese Patent Post-Exam Publication JP-B-60-11986, etc.). Also, processes such as disclosed in Japanese Patent Unexamined Publication JP-A-54-56630 and JP-A-58-120673 have been proposed for forming a pigment from its crude obtained according to the above process.

This pigment crude, however, is poor in dispersibility and requires strong dispersion for preparation of pigment, so that production efficiency is low and it is difficult to obtain a high-quality pigment from this crude. It has been proposed to pulverize the crude with a surfactant or a coloring matter derivative for a dispersion (JP-A-2-102272, JP-A-2-102273, U.S. Pat. No. 5,275,654, etc.). This method, however, still involves many problems such as low production efficiency, insufficient atomization and poor dispersion stability.

SUMMARY OF THE INVENTION

With the aim of solving the above problems, the present inventors have conducted extensive studies. As a result, it has been found that an excellent pigment crude can be obtained by subjecting a compound of the formula (2) shown below to a ring closure reaction in the presence of a derivative of a dioxazine compound of the formula (3) shown below.

Thus, the present invention provides:

(1) A process for producing a dioxazine compound represented by the formula (1):

wherein R represents a hydrogen atom or an alkyl group having 1–8 carbon atoms; and each of $Z^1$ and $Z^2$ independently represents a hydrogen atom or a halogen atom, which comprises subjecting a compound represented by the formula (2):

wherein R, $Z^1$ and $Z^2$ are as defined above, to a ring closure reaction in the presence of a compound represented by the formula (3)

wherein R' represents a hydrogen atom or an alkyl group having 1 to 8 carbon atoms; each of $Z^3$ and $Z^4$ independently represents a hydrogen atom or a halogen atom; each of X and Y independently represents a substituent; i is a number of 0 to 6; and j is a number of 0 to 6, but i+j=1 to 6.

(2) A process for preparing a dioxazine compound described in (1) above, wherein in the formula (3) the substituent of X is —A—$(CH_2)_l$—B, the substituent of Y is A'—$(CH_2)_n$—B' (wherein each of A and A' independently represents a direct bond or a divalent bonding group selected from —$SO_2$—, —CO—, —S—, —$CH_2NHCO$—, —O—, —$CR^1R^2$—, —$CONR^3$—, —$SO_2NR^4$— and —$NR^5$— (wherein each of $R^1$, $R^2$, $R^3$, $R^4$ and $R^5$ independently represents a hydrogen atom or a saturated or unsaturated aliphatic or aromatic group which may contain a chalcogen atom, a nitrogen atom and/or a halogen atom), each of B and B' independently represents a hydrogen atom or a bonding group selected from —$OR^6$ (wherein $R^6$ is a hydrogen atom, a metal atom or a saturated or unsaturated aliphatic or aromatic group which may contain a chalcogen atom, a nitrogen atom and/or a halogen atom), —$NR^7R^8$ and —$R^9$ (wherein each of $R^7$, $R^8$ and $R^9$ independently represents a hydrogen atom or a saturated or unsaturated aliphatic or aromatic group which may contain a chalcogen atom, a nitrogen atom and/or a halogen atom), and each of n and l independently represents a number of 0 to 8)); i is a number of 0 to 6; and j is a number of 0 to 6.

(3) A process for preparing a dioxazine compound described in (2) above, wherein A is —$SO_2$— or —$SO_2NR^4$—; l is a number of 0 to 8; B is —$OR^6$, —$NR^7R^8$ or —$R^9$; A' is —$SO_2$—, n is 0; B' is —$OR^6$; i is a number of 1 to 6; and j is a number of 0 to 5.

(4) A process for preparing a dioxazine compound described in (2) above, wherein A is —O—, —$CR^1R^2$—, —$CH_2NHCO$— or —$CONR^3$—; l is a number of 0 to 8; B is a hydrogen atom or a bonding group selected from —$OR^6$, —$NR^7R^8$ or —$R^9$; i is a number of 1 to 6; and j is 0.

(5) A process for preparing a dioxazine compound described in (1) above, wherein the compound of the formula (3) is a sulfonic acid derivative, a sulfonamide derivative, an alkylether derivative, an alkylamide derivative or a carbonamide derivative of the compound of the formula (1).

(6) A process for producing a dioxazine compound described in (5) above, wherein the sulfonic acid derivative is a compound in which —$SO_3M$ (M being a hydrogen atom or a metal atom) is bonded to the compound of the formula (1), the sulfonamide derivative is a compound in which an alkylaminosulfonyl group, an alkylaminoalkylaminosulfonyl group or a group represented by the formula —$SO_2N(R_{11})_2$ (wherein $R_{11}$ is $(CH_2CH_2O)_nH$ (n being a number of 1 to 30) are bonded to the compound of the formula (1), the alkylether derivative is a compound in which an alkoxy group having 1–8 carbon atoms is bonded to the compound of the formula (1), the alkylamide derivative is a compound in which a phthalimidoalkyl group, an oniumalkylcarbonylaminoalkyl group, an alkylcarbonylaminoalkyl group or an alkylaminoalkylcarbonylaminoalkyl group are bonded to the compound of the formula (1), and the carbonamide derivative is a compound in which an alkylaminocarbonyl group or an alkylaminoalkylaminocarbonyl group are bonded to the compound of the formula (1).

(7) A process for preparing a dioxazine compound described in (1) above, wherein the compound of the formula (3) is a sulfonic acid derivative of the compound of the formula (1).

(8) A process for preparing a dioxazine compound described in (7) above, wherein the sulfonic acid derivative is a compound in which 1 to 6 sulfonic groups are bonded as substituents to the compound of the formula (1), a part or whole thereof being reduced to salts.

(9) A process for preparing a dioxazine compound described in (1) above, wherein the compound of the formula (3) is a sulfonamide derivative of the compound of the formula (1).

(10) A process for preparing a dioxazine compound described in (9) above, wherein the sulfonamide derivative is a compound in which 1 to 5 alkylaminosulfonyl groups, alkylaminoalkylaminosulfonyl groups or groups of the formula $SO_2N(R_{11})$ (wherein $R_{11}$ is $(CH_2CH_2O)_nH$ (n being a number of 1 to 30)) and 0 to 3 sulfonic groups or salts thereof (the total number of substituents being 1 to 6) are bonded as substituents to the compound of the formula (1).

(11) A process for preparing a dioxazine compound described in (1) above, wherein the compound of the formula (3) is an alkylamide derivative of the compound of the formula (1).

(12) A process for preparing a dioxazine compound described in (11) above, wherein the alkylamide derivative is a compound in which 1 to 5 oniumalkylcarbonylaminoalkyl group and 0 to 3 sulfonic groups or salts thereof (the total number of substituents being 1 to 6) are bonded as substituents to the compound of the formula (1).

(13) A process for preparing a dioxazine compound described in (12) above, wherein the oniumalkylcarbonylaminoalkyl group is a pyridiniumalkylcarbonylaminoalkyl group and the pair ion is chloride ion, lactic ion or methylsulfuric ion.

(14) A process for preparing a dioxazine compound described in (8), (10) or (12) above, wherein the salt is an alkaline metal salt.

(15) A process for preparing a dioxazine compound described in (1) above, wherein the amount of the compound of the formula (3) used falls within the range of from 0.005 to 0.3 part by weight per 1 part by weight of the compound of the formula (2).

(16) A process for preparing a dioxazine compound described in (1), (5), (7), (9) or (11) above, wherein the ring closure reaction is carried out under heating at a temperature of from 100° to 200° C. in the presence of the compound of the formula (3) in an amount of 0.005 to 0.3 part by weight per 1 part by weight of the compound of the formula (2) and a ring-closing agent.

(17) A process for preparing a dioxazine compound described in (16) above, wherein the amount of the ring-closing agent used falls within the range of from 0.1 to 5 moles per 1 mole of the compound of the formula (2).

(18) Colored materials comprising the compound of the formula (1) synthesized according to the process of (1) above.

(19) A dioxazine compound represented by the formula (1) set forth in (1) above having a plate-like crystal form having a vertical and horizontal ratio of 1:1 to 1:4 in the mean value of crystal size.

(20) Colored materials comprising a reaction product which is obtained by the reaction set forth in (1) above.

(21) A reaction product in a plate-like crystal form which is obtained by the reaction set forth in (1) above.

DETAILED DESCRIPTION OF THE INVENTION

In the present invention, ring closure reaction of a compound of the formula (2) is carried out in the presence of a compound of the formula (3). In the formula (3), R' represents a hydrogen atom or an alkyl group having 1 to 8 carbon atoms. Examples of the alkyl groups having 1–8 carbon atoms represented by R' are methyl, ethyl, n-propyl, isopropyl, n-butyl, isobutyl,t-butyl, pentyl, hexyl, heptyl and octyl. Among these groups, methyl, ethyl, n-propyl, isopropyl, n-butyl, isobutyl and t-butyl are preferred. Also in the formula (3), each of i and j is a number of 0 to 6 provided that i+j=1 to 6, and each of $Z^3$ and $Z^4$ independently represents a hydrogen atom or a halogen atom. The halogen atom represented by $Z^3$ and $Z^4$ includes chlorine atom and bromine atom, the former being preferred.

X and Y in the formula (3) are substituents. A typical example of the substituents represented by X is —A—$(CH_2)_i$—B, and an example of the substituents represented by Y is —A'—$(CH_2)_n$—B' (wherein each of A and A' independently represents a direct bond or a divalent bonding group selected from —$SO_2$—, —CO—, —S—, —$CH_2NHCO$—, —O—, —$CR^1R^2$—, —$CONR^3$—, —$SO_2NR^4$—and —$NR^5$— (wherein each of $R^1$, $R^2$, $R^3$, $R^4$ and $R^5$ independently represents a hydrogen atom or a saturated or unsaturated aliphatic or aromatic group which may contain a chalcogen atom, a nitrogen atom and/or a halogen atom), and each of B and B' independently represents a hydrogen atom or a bonding group selected from —$OR^6$ ($R^6$ representing a hydrogen atom, a metal atom or a saturated or unsaturated aliphatic or aromatic group which may contain a chalcogen atom, a nitrogen atom and/or a halogen atom), —$NR^7R^8$ and —$R^9$ (wherein each of $R^7$, $R^8$ and $R^9$ independently represents a hydrogen atom or a saturated or unsaturated aliphatic or aromatic group which may contain a chalcogen atom, a nitrogen atom and/or a halogen atom). The metal atom is preferably an alkaline metal atom such as lithium, sodium or potassium atom, and the chalcogen atom is preferably oxygen or sulfur atom. Exemplary of the saturated or unsaturated aliphatic or aromatic groups which may contain a chalcogen atom, a nitrogen atom and/or a halogen atom are alkyl group, alkenyl group, cycloalkyl group, ester group, ether group, acyl group, aryl group, pyridinium group, chloropyridinium group, pyridyl group, pyridonyl group, piperidonyl group, morpholino group, furyl group, oxazolyl group, thienyl group, chlorobenzyl group and nitrobenzyl group.

Examples of the substituents represented by X and Y are —$SO_3M$ (M being a hydrogen atom or a metal atom), alkylaminosulfonyl group, alkylaminoalkylaminosulfonyl group, $C_{1-8}$ alkoxy group, phthalimidoalkyl group, oniumalkylcarbonylaminoalkyl group, alkylcarbonylaminoalkyl group, alkylaminoalkylcarbonylaminoalkyl group, —$SO_2N(R_{11})_2$ (wherein $R_{11}$ represents $(CH_2CH_2O)_nH$ (n being an integer of 1 to 30), alkylaminocarbonyl group and alkylaminoalkylaminocarbonyl group.

M in —$SO_3M$ represents a hydrogen atom or a metal atom, for example, an alkaline metal atom such as lithium, sodium or potassium atom, or an alkaline earth metal atom such as magnesium or calcium atom. M is preferably a hydrogen atom or an alkaline metal atom, more preferably a hydrogen, sodium or potassium atom. Examples of —$SO_3M$ include sulfonic acid, lithium sulfonate, sodium sulfonate, potassium sulfonate, magnesium sulfonate and calcium sulfonate.

Examples of the alkylaminosulfonyl groups are ($C_0$–$C_4$) alkylaminosulfonyl groups such as N-methylaminosulfonyl group and N-ethylaminosulfonyl group, and di($C_0$–$C_4$) alkylaminosulfonyl groups such as N-ethyl-N-methylaminosulfonyl group, dimethylaminosulfonyl group and dipropylaminosulfonyl group. Examples of alkylaminoalkylaminosulfonyl groups are ($C_0$–$C_4$)alkylamino($C_0$–$C_4$)alkylaminosulfonyl groups such as N-methylaminopropylaminosulfonyl and N-ethylaminopropylaminosulfonyl, and di($C_0$–$C_4$) alkylamino($C_0$–$C_4$)alkylaminosulfonyl groups such as dimethylaminopropylaminosulfonyl, diethylaminopropylaminosulfonyl, dimethylaminomethylaminosulfonyl, diethylaminomethylaminosulfonyl, diethylaminoethylaminosulfonyl, di(n-propyl)-aminomethylaminosulfonyl, di(n-propyl)aminoethylaminosulfonyl, di(n-propyl)aminopropylaminosulfonyl, di(isopropyl)aminomethylaminosulfonyl, di(isopropyl)-aminoethylaminosulfonyl, di(isopropyl)aminopropylaminosulfonyl, dibutylaminopropylaminosulfonyl, and N-ethyl-N-methylaminopropylaminosulfonyl.

Examples of $C_{1-8}$ alkoxy groups are methoxy, ethoxy, n-propoxy, isopropoxy, n-butoxy, sec-butoxy, t-butoxy, pentyloxy, hexyloxy, heptyloxy and octyloxy. Examples of phthalimidoalkyl groups are phthalimido-($C_0$–$C_4$)alkyl groups such as phthalimidomethyl, nitrophthalimidomethyl, monochlorophthalimidomethyl and dichlorophthalimidomethyl. Examples of oniumalkycarbonylaminoalkyl groups are pyridiniumalkylcarbonylaminialkyl group and tetraalkylammoniumalkylcarbonylaminoalkyl group. Examples of pyridiniumalkylcarbonylaminoalkyl groups are pyridinium ($C_0$–$C_4$)-alkylcarbonylamino($C_0$–$C_4$)alkyl groups such as pyridiniummethylcarbonylaminomethyl. Examples of tetraalkylammoniumalkylcarbonylaminoalkyl groups are tetra($C_0$–$C_4$)alkylammonium($C_0$–$C_4$)alkylcarbonylamino ($C_0$–$C_4$)alkyl groups such as tetramethylammoniummethylcarbonylaminomethyl group. Examples of pair ions of onium are non-color development ions, for example, halogen ions such as a fluorine ion, a chlorine ion, a bromide ion and an iodine ion, sulfonic ions such as a sulfuric ion, methylsulfuric ion, a benzenesulfonic ion and methanesulfonic ion, fatty acid ions such as acetic ion, and lactic ions such as oxy acid ion and benzoic ion. Examples of —$SO_2N(R_{11})$ are diethanolaminosulfonyl and di(polyethyleneglycol)aminosulfonyl groups. The polymerization degree of polyethylene glycol is about 1 to 30, preferably about 20 to 30. Examples of alkylcarbonylaminoalkyl groups are ($C_0$–$C_4$)alkylcarbonylamino($C_0$–$C_4$) alkyl groups such as methylcarbonylaminopropyl and ethylcarbonylaminobutyl. Examples of alkylaminoalkylcarbonylaminoalkyl groups are ($C_0$–$C_4$) alkylcarbonylamino($C_0$–$C_4$)alkyl groups such as dimethylaminopropylcarbonylaminopropyl and ethylaminomethylcarbonylaminobutyl. Examples of dialkylaminoalkylaminocarbonyl groups are dimethylaminopropylaminocarbonyl, diethylaminopropylaminocarbonyl, and N-methyl-N-propylaminopropylaminocarbonyl.

Preferred combinations of R', $Z^3$, $Z^4$, X and Y in the formula (3) are the ones in which, for example, R' is a methyl, ethyl or propyl group, $Z^3$ is a hydrogen or chlorine atom, $Z^4$ is a hydrogen or chlorine atom, X is a salt of sulfonic group, an alkylaminoalkylaminosulfonyl group or oniumalkylcarbonylaminoalkyl group, and Y is a sulfonic group. Both i and j in the formula (3) are a number of 0 to 5, but i+j=1 to 6.

The compounds of the formula (3) may be defined as the following compounds. That is, the compounds of the formula (3) includes sulfonic acid derivatives, sulfonamide derivatives, alkylether derivatives, alkylamide derivatives or carbonamide derivatives of the compounds of the formula (1). Examples of sulfonic acid derivatives include a compound in which —$SO_3M$ (M being a hydrogen atom or a metal atom) are bonded as substituent to the compound of the formula (1). Examples of sulfonamide derivatives include compounds in which an alkylaminosulfonyl group, an alkylaminoalkylaminosulfonyl group or a group of the formula —$SO_2N(R_{11})$ (wherein $R_{11}$ is $(CH_2CH_2O)_nH$ (n being an integer of 1 to 30)) are bonded as substituent to the compound of the formula (1). Examples of alkylether derivatives include a compound in which a $C_{1-8}$ alkoxy group is bonded as substituent to the compound of the formula (1). Examples of alkylamide derivatives include compounds in which a phthalimidoalkyl group, an oniumalkylcarbonylaminoalkyl group, an alkylcarbonylaminoalkyl group or an alkylaminoalkylcarbonylaminoalkyl group are bonded as substituent to the compound of the formula (1). Examples of carbonamide derivatives include compounds in which an alkylaminocarbonyl group or an alkylaminoalkylaminocarbonyl group are bonded as substituent to the compound of the formula (1).

Among these compounds of the formula (3), alkylamide derivatives, sulfonic acid derivatives and sulfonamide derivatives of the compounds of the formula (1) are preferred. Examples of the sulfonic acid derivatives include a compound in which 1 to 6 sulfonic groups are bonded as substituent to the compound of the formula (1), a part or whole thereof being reduced to salts. Examples of the sulfonamide derivatives include a compound in which 1 to 5 alkylaminosulfonyl groups, alkylaminoalkylaminosulfonyl groups or groups of the formula —$SO_2N(R_{11})_2$ (wherein $R_{11}$ is $(CH_2CH_2O)_nH$ (n being an integer of 1 to 30)), and 0 to 3 sulfonic groups or salts thereof (the total number of substituents being 1 to 6) are bonded as substituent to the compound of the formula (1), preferably a compound in which 1 to 5 alkylaminoalkylaminosulfonyl groups and 0 to 3 sulfonic groups or salts thereof (the total number of the substituents being 1 to 6) are bonded to the compound of the formula (1). Examples of alkylamide derivatives of compounds of the formula (1) include compounds of the formula (1), to which 1 to 5 oniumalkylcarbonylaminoalkyl groups and 0 to 3 sulfonic groups or salts thereof (total number of substituents are 1 to 6), preferably 1 to 5 pyridiniumalkylcarbonylaminoalkyl groups, and 0 to 3 sulfonic groups or salts thereof (total number of substituents are 1 to 6) are bonded. In this case, the pair ion includes preferably chlorine ion, methylsulfuric ion, acetic ion and lactic ion.

Typical examples of the compounds of the formula (3) are shown below:

(7)

(8)

(9)

(10)

(11)

(12)

(13)

-continued

(14)

(15)

(16)

(17)

(18)

(19)

(20)

-continued (21)

(22)

(23)

(24)

In the present invention, a compound of the formula (2) is used as starting material for obtaining a compound of the formula (1). In the formula (1) and (2), R is a hydrogen atom or an alkyl group having 1 to 8 carbon atoms. Examples of the alkyl groups having 1 to 8 carbon atoms represented by R are methyl, ethyl, n-propyl, isopropyl, n-butyl, isobutyl, t-butyl, pentyl, hexyl, heptyl and octyl. Each of $Z^1$ and $Z^2$ independently represents a hydrogen atom or a halogen atom such as chlorine atom or bromine atom, chlorine atom being preferred.

An easily dispersible dioxazine compound of the formula (1) can be obtained by subjecting the compound of the formula (2) to a ring closure reaction at an elevated temperature in the presence of the compound of the formula (3) and if desired a ring-closing agent in an inert organic solvent. The reaction system may be heated under a reduced pressure. The amount of the compound of the formula (3) used falls within the range of from preferably about 0.005 to 0.3 part by weight, more preferably about 0.01 to 0.2 part by weight, per 1 part by weight of the compound of the formula (2). The compound of the formula (3) used in this invention may be a mixture of the compounds differing in number and type of substituents. The compound may be in the form of powder, a solution of aqueous, organic acid or organic solvent etc., or wet cake.

Ring closure reaction time falls within the range of from preferably 0.5 to 6 hours, more preferably 1 to 5 hours, and reaction temperature falls within the range of from preferably 100° to 200° C., more preferably 150° to 180° C. The inert solvent used for the above reaction includes halogenated aromatic solvents such as chlorobenzene, dichlorobenzene, trichlorobenzene, bromobenzene, dibromobenzene, chloronaphthalene, chlorotoluene, dichlorotoluene and bromotoluene; alkylated aromatic solvents such as alkylbenzenes (toluene, xylene, mesitylene, ethylbenzene and diethylbenzene) and methylnaphthalene; nitrobenzene; alkanes and alkenes such as decane, dodecane, decene and dodecene. These solvents may be used either singly or as a mixture. The amount of the solvent used falls within the range of from preferably 3 to 20 parts by weight, more preferably about 5 to 15 parts by weight, per 1 part by weight of the compound of the formula (2).

As ring-closing agent, there can be used sulfonic acid halides such as benzenesulfonyl chloride, toluenesulfonyl chloride, chlorobenzenesulfonyl chloride and nitrobenzenesulfonyl chloride, acid halides such as benzoyl chloride, and halides such as chloranil and dichloronaphthoquinone. Among these compounds, benzenesulfonyl chloride, p-toluenesulfonyl chloride, m-nitrobenzenesulfonyl chloride, chlorobenzenesulfonyl chloride and the like are preferred. In case a ring-closing agent is used, its amount used falls within the range of from preferably 0.1 to 5 moles, more preferably about 0.5 to 3 moles per 1 mole of the compound of the formula (2).

After the reaction is completed, the solution containing the dioxazine compound obtained by this invention is filtered to separate the objective substance. If necessary, the produced crystals may be washed with a solvent.

It is also embraced in the concept of this invention to condense a compound of the formula (5):

(5)

(wherein R is as defined above) and chloranil in an inert solvent such as mentioned above in the presence of an acid coupling agent to obtain a compound of the formula (2) and apply this compound directly to the process of the present invention. As acid coupling agent, there can be used organic or inorganic alkalis, for example, weakly acidic alkali metal salts such as sodium carbonate and sodium acetate, and trialkylamines such as trimethylamine and triethylamine. In this case, a compound of the formula (3) may be added prior to the condensation reaction of the compound of the formula (5) and chloranil.

Figure 1:
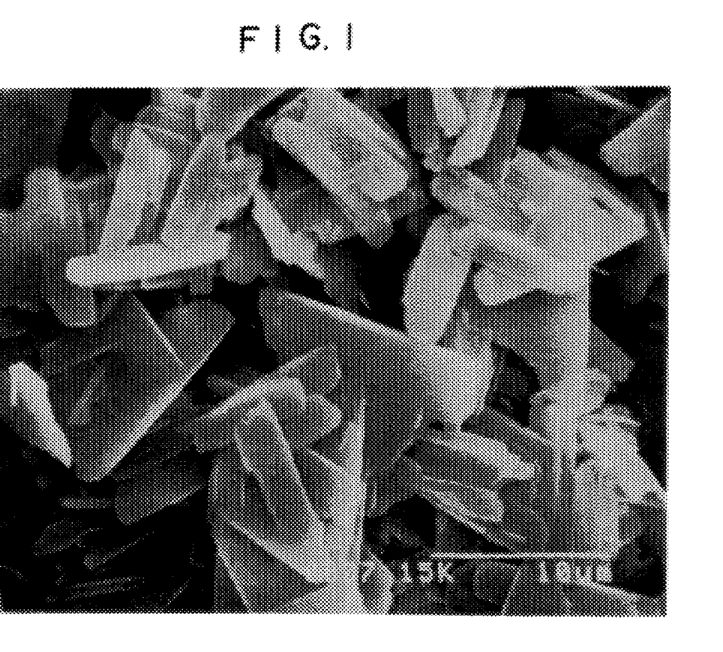
FIG. 1 is an electron micrograph (3,000× magnification) of dioxazine crystals produced according to the process of Example 1.
Figure 2:
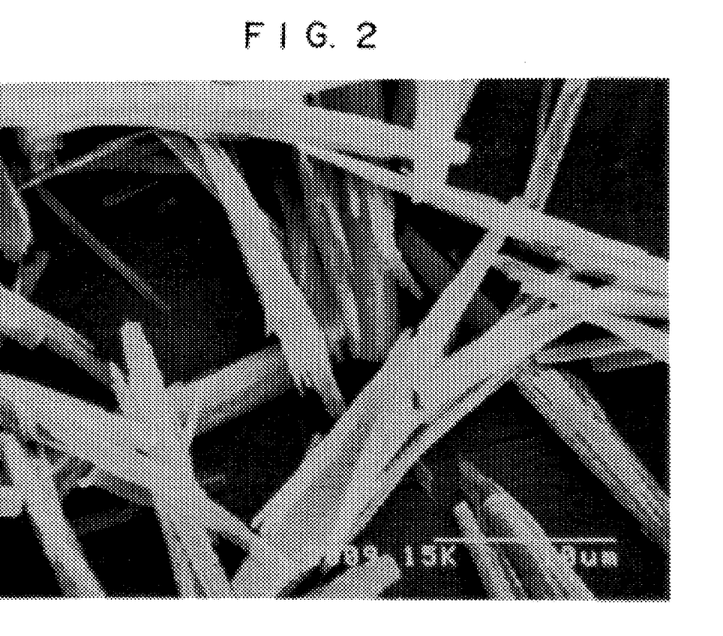
FIG. 2 is an electron micrograph (3,000× magnification) of dioxazine crystals produced according to the process of Comparative Example 1.

A dioxazine compound having a plate-like crystal form of the present invention has thin plate-like crystal form as seen from the electron micrograph of FIG. 1. The plate-like crystal has a horizontal and vertical ratio of about 1:1 to 1:5, preferably 1:1 to 1:4 in the mean value of crystal size. The dioxazine crystals obtained according to the conventional processes are needles or prisms as seen in the electron micrograph of FIG. 2 and clearly different from the plate-like crystal from of the present invention. These plate-like crystal form can be obtained by subjecting the compound of the formula (2) to a ring closure reaction in the presence of a dioxazine compound derivative of the formula (6) having a sulfonyl group shown below (the compound of the formula (3) in which X is a sulfonic group such as $SO_3H$ or $SO_3Na$, $Z^3$ and $Z^4$ are independently a hydrogen atom or a halogen atom, i is a number of 1 to 6, and j is 0).

sulfuric acid; a process of chlorosulfonating a dioxazine compound of the formula (1) and then reacting with an amine compound; a process of chloromethylating a dioxazine compound of the formula (1) and then reacting with an amine compound (JP-A-1-217078, etc.); a process of chloroacetoaminomethylating a dioxazine compound of the formula (1) and then reacting with an amine; a process of reacting a dioxazine compound of the formula (1) with N-methylolphthalimide in polyphosphoric acid (JP-A-4-246469, etc.).

EXAMPLES

The present invention is further illustrated with reference to the following examples, which examples however are merely intended to be illustrative and not to be construed as limiting the scope of the invention. In the following Examples, all "%" and "parts" are based on "by weight" unless otherwise noted.

Example 1

To a mixture of 20 parts of 2,5-dichloro-3,6-bis(9-ethyl-3-carbazolylamino)-1,4-benzoquinone and 120 parts of o-dichlorobenzene, 0.5 parts of a compound of the formula (7) (a compound of the formula (6) in which R' is ethyl, $Z^3$ and $Z^4$ are chlorine, M is sodium, and i is 2) was added. The mixture was heated to 140°–150° C. under a reduced pressure and then 8 parts of p-toluenesulfonyl chloride was added at the same temperature, followed by stirring at 165°–175° C. for 5 hours. The reaction mixture was cooled and produced crystals were filtered, washed with o-dichlorobenzene, methanol and water in that order and dried to give 17.5 parts of a dioxazine compound (a compound of the formula (1) wherein R is ethyl, and $Z^1$ and $Z^2$ are chlorine atom) in a plate-like crystal form.

Example 2

10 parts of 3-amino-9-ethylcarbazole, 7 parts of chloranil, 4 parts of sodium carbonate and 100 parts of (6)

The colored materials of the present invention include, for example, inks, paints, synthetic resin films, synthetic resin plates, masterbatches made of synthetic resins, fibers, rubbers, pigment printing pastes, pigment printing dispersions and the like which have been colored with the compound of the formula (1) obtained according to the process of the present invention.

The dioxazine compounds obtained according to the process of the present invention are useful as a coloring matter for pigment. Specifically, these dioxazine compounds (pigment crude) are very suited as a coloring pigment for polymeric materials. When this pigment crude is worked into a pigment in the usual way and used for coloring of ink, paint, resin, etc., or for pigment printing, there can be obtained excellent fastness properties such as light resistance, heat resistance and migration resistance, good fluidity and gloss of pigment, high coloring power, high dispersion stability, and unlikeliness of re-coagulation.

The compounds of the formula (3) can be produced by the known processes such as mentioned below: a process of sulfonating a dioxazine compound of the formula (1) with o-dichlorobenzene were mixed and stirred at 30°–65° C. for a reaction. On completion of condensation reaction, 1.5 parts of a compound of the formula (7) was added and the mixture was heated to 140°–150° C. under a reduced pressure, followed by adding 7 parts of p-toluenesulfonyl chloride at the same temperature and stirring at 165°–175° C. for 5 hours. The reaction product was cooled and the produced crystals were filtered, washed with o-dichlorobenzene, methanol and water in that order and dried to give 12.8 parts of a dioxazine compound (a compound of the formula (1) wherein R is ethyl, and $Z^1$ and $Z^2$ are chlorine atom) in a plate-like crystal form.

Example 3

To a mixture of 20 parts of 2,5-dichloro-3,6-bis(9-ethyl-3-carbazolylamino)-1,4-benzoquinone and 120 parts of o-dichlorobenzene, 2 parts of a compound of the formula (8) (a compound of the formula (6) wherein R' is ethyl, $Z^3$ and $Z^4$ are chlorine atom, M is sodium, and i is 1) and 8 parts of p-toluenesulfonyl chloride were added and stirred at 165°–175° C. for 5 hours for a reaction. On completion of the reaction, the reaction product was cooled and produced crystals were filtered, washed with o-dichlorobenzene, methanol and water in that order and dried to give 17.3 parts of a dioxazine compound (a compound of the formula (1) wherein R is ethyl, and $Z^1$ and $Z^2$ are chlorine atom).

Example 4

10 parts of 3-amino-9-ethylcarbazole, 8 parts of chloranil, 3 parts of sodium carbonate and 100 parts of o-dichlorobenzene were mixed and stirred at 25°–60° C. for a reaction. After completion of condensation reaction, 2 parts of a compound of the formula (8) and 6 parts of p-toluenesulfonyl chloride were added and stirred at 165°–175° C. for 5 hours for a reaction. On completion of the reaction, the reaction product was cooled and produced crystals were filtered, washed with o-dichlorobenzene, methanol and water in that order and dried to give 13.2 parts of a dioxazine compound (a compound of the formula (1) wherein R is ethyl, and $Z^1$ and $Z^2$ are chlorine atom).

Example 5

14 parts of 3-amino-9-octylcarbazole, 8 parts of chloranil, 3 parts of sodium carbonate and 100 parts of o-dichlorobenzene were mixed and stirred at 25°–60° C. for a reaction. On completion of condensation reaction, 0.3 part of a compound of the formula (7) was added and the mixture was heated to 140°–150° C., followed by further adding 6 parts of benzenesulfonyl chloride and stirring at 165°–175° C. for 5 hours for a reaction. On completion of the reaction, the reaction product was cooled and precipitated crystals were filtered, washed with o-dichlorobenzene, methanol and water in that order and dried to give 14.2 parts of a dioxazine compound (a compound of the formula (1) wherein R is octyl, and $Z^1$ and $Z^2$ are chlorine atom) in a plate-like crystal form.

Example 6

10 parts of 3-amino-9-ethylcarbazole, 8 parts of chloranil, 3 parts of sodium carbonate, 2 parts of a compound of the formula (7) in wet cake form and 100 parts of o-dichlorobenzene were mixed and stirred at 25°–60° C. for a reaction. On completion of condensation reaction, the reaction mixture was heated to 140° C., followed by adding 6 parts of p-toluenesulfonyl chloride and stirring at 165°–175° C. for 3 hours for a reaction. On completion of the reaction, the reaction product was cooled and produced crystals were filtered, washed with o-dichlorobenzene, methanol and water in that order and dried to give 12.8 parts of a dioxazine compound (a compound of the formula (1) wherein R is ethyl, and $Z^1$ and $Z^2$ are chlorine atom) in a plate-like crystal form.

Example 7

To a mixture of 20 parts of 2,5-dichloro-3,6-bis(9-ethyl-3-carbazolylamino)-1,4-benzoquinone and 120 parts of o-dichlorobenzene were added an aqueous solution of a mixture of 0.1 part of a compound of the formula (7) and a compound of the formula (9) (a compound of the formula (6) wherein R is ethyl, $Z^3$ and $Z^4$ are chlorine atom, M is sodium, and i is 3). The mixture was gradually heated to 140°–150° C. under a reduced pressure. Then 8 parts of p-toluenesulfonyl chloride was added at the same temperature and the mixture was stirred at 165°–175° C. for 5 hours for reaction. On completion of the reaction, the reaction product was cooled and produced crystals were filtered, washed with o-dichlorobenzene, methanol and water in that order and dried to give 17.5 parts of a dioxazine compound (a compound of the formula (1) wherein R is ethyl, and $Z^1$ and $Z^2$ are chlorine atom) in a plate-like crystal form.

Example 8

10 parts of 3-amino-9-ethylcarbazole, 6.5 parts of chloranil, 3 parts of sodium carbonate, and an aqueous solution of a mixture of 0.1 part of a compound of the formula (7), 0.7 part of a compound of the formula (9), 0.2 part of a compound of the formula (10) (a compound of the formula (6) wherein R' is ethyl, $Z^3$ and $Z^4$ are chlorine atom, M is sodium and i is 4) and 0.1 part of a compound of the formula (11) (a compound of the formula (6) wherein R' is ethyl, $Z^3$ and $Z^4$ are chlorine atom, M is sodium, and i is 5) was mixed with 100 parts of o-dichlorobenzene and stirred at 30°–65° C. for a reaction. On completion of condensation reaction, the reaction mixture was heated to 140°–150° C. under a reduced pressure, followed by adding 6 parts of p-toluenesulfonylchloride at the same temperature and stirring at 165°–175° C. for 2 hours for a reaction. On completion of the reaction, the reaction product was cooled and obtained crystals were filtered, washed with o-dichlorobenzene, methanol and water in that order and dried to give 12.6 parts of a dioxazine compound (a compound of the formula (1) wherein R is ethyl, and $Z^1$ and $Z^2$ are chlorine atom) in a plate-like crystal form.

Example 9

To a mixture of 20 parts of 2,5-dichloro-3,6-bis(9-ethyl-3-carbazolylamino)-1,4-benzoquinone and 120 parts of o-dichlorobenzene, an acetic acid solution of 0.8 part of a compound of the formula (12) (a compound of the formula (3) wherein R' is ethyl, $Z^3$ and $Z^4$ are chlorine atom, X is $SO_2NH(CH_2)_3N(CH_3)_2$, i is 3, and j is 0) was added, and the mixture was heated to 140°–150° C. under a reduced pressure, followed by adding 8 parts of p-toluenesulfonyl chloride at the same temperature and stirring at 165°–175° C. for 3 hours for a reaction. On completion of the reaction, the reaction product was cooled and produced crystals were filtered, washed with o-dichlorobenzene, methanol and water in that order and dried to give 17.4 parts of a dioxazine compound (a compound of the formula (1) wherein R is ethyl, and $Z^1$ and $Z^2$ are chlorine atom).

Example 10

10 parts of 3-amino-9-ethylcarbazole, 7 parts of chloranil, 2.8 parts of sodium carbonate and 100 parts of o-dichlorobenzene were mixed and stirred at 30°–65° C. for a reaction. On completion of condensation reaction, 1.5 parts of a compound of the formula (13) (a compound of the formula (3) wherein R' is ethyl, $Z^3$ and $Z^4$ are chlorine atom, X is $SO_2NH(CH_2)_3N(C_2H_5)_2$, i is 3, and j is 0) in wet cake form were added, and the mixture was heated to 140°–150° C. under a reduced pressure. Then 6 parts of benzenesulfonyl chloride was added at the same temperature and the mixture was stirred at 165°–175° C. for 5 hours for a reaction. On completion of the reaction, the reaction product was cooled and produced crystals were filtered, washed with o-dichlorobenzene, methanol and water in that order and dried to give 12.4 parts of a dioxazine compound (a compound of the formula (1) wherein R is ethyl, and $Z^1$ and $Z^2$ are chlorine atom).

Example 11

To a mixture of 20 parts of 2,5-dichloro-3,6-(bis(9-ethyl-3-carbazolylamino)-1,4-benzoquinone and 120 parts of o-dichlorobenzene was added an aqueous solution of a mixture of 0.2 part of a compound of the formula (7), 0.4 part of a compound of the formula (9), and 0.5 part of a compound of the formula (14) (a compound of the formula (3) wherein R' is ethyl, $Z^3$ and $Z^4$ are chlorine atom, X is $SO_2NH(CH_2)_3N(CH_3)_2$, i is 4, and j is 0). The resulting mixture was heated to 140°–150° C. under a reduced pressure, followed by adding 8 parts of p-toluenesulfonyl chloride at the same temperature and stirring at 165°–175° C. for 5 hours for a reaction. On completion of the reaction, the reaction product was cooled and produced crystals were filtered, washed with o-dichlorobenzene, methanol and water in that order and dried to give 17.5 parts of a dioxazine compound (a compound of the formula (1) wherein R is ethyl, and $Z^1$ and $Z^2$ are chlorine atom).

Example 12

10 parts of 3-amino-9-ethylcarbazole, 7 parts of chloranil, 3 parts of sodium carbonate and 100 parts of o-dichlorobenzene were mixed and stirred at 30°–65° C. for a reaction. On completion of condensation reaction, an acetic acid solution of 1.0 part of a compound of the formula (15) (a compound of the formula (3) wherein R' is ethyl, $Z^3$ and $Z^4$ are chlorine atom, X is $SO_2NH(CH_2)_3N(CH_3)_2$, Y is $SO_3H$, i is 3 and j is 1) was added and the mixture was heated to 140°–150° under a reduced pressure, followed by adding 7 parts of p-toluenesulfonyl chloride at the same temperature and stirring at 165°–175° for 2 hours for a reaction. On completion of the reaction, the reaction product was cooled and produced crystals were filtered, washed with o-dichlorobenzene, methanol and water in that order and dried to give 12.6 parts of a dioxazine compound (a compound of the formula (1) wherein R is ethyl, and $Z^1$ and $Z^2$ are chlorine atom).

Example 13

10 parts of 3-amino-9-ethylcarbazole, 6 parts of chloranil, 4 parts of sodium carbonate, 0.5 part of a compound of the formula (16) (a compound of the formula (3) wherein R' is ethyl, $Z^3$ and $Z^4$ are chlorine atom, X is $SO_2NH(CH_2)_3N(CH_3)_2$, Y is $SO_3H$, i is 2, and j is 2) in wet cake form and 100 parts of o-dichlorobenzene were mixed and stirred at 30°–65° C. for a reaction. On completion of condensation reaction, the reaction mixture was heated to 140°–150° C. under a reduced pressure, followed by adding 7 parts of p-toluenesulfonyl chloride at the same temperature and stirring at 165°–175° C. for 5 hours for a reaction. On completion of the reaction, the reaction product was cooled and produced crystals were filtered, washed with o-dichlorobenzene, methanol and water in that order and dried to give 12.3 parts of a dioxazine compound (a compound of the formula (1) wherein R is ethyl and $Z^1$ and $Z^2$ are chlorine atom).

Example 14

10 parts of 3-amino-9-ethylcarbazole, 7 parts of chloranil, 3 parts of sodium carbonate, 1.5 parts of a compound of the formula (17) (a compound of the formula (3) wherein R' is ethyl, $Z^3$ and $Z^4$ are chlorine atom, X is $OC_8N_{17}$, i is 2 and j is 0) and 100 parts of o-dichlorobenzene were mixed and stirred at 30°–65° C. for a reaction. On completion of condensation reaction, the reaction mixture was heated to 140°–150° C. under a reduced pressure, followed by adding 6 parts of benzenesulfonyl chloride at the same temperature and stirring at 165°–175° C. for 5 hours for a reaction. On completion of the reaction, the reaction product was cooled and produced crystals were filtered, washed with o-dichlorobenzene, methanol and water in that order and dried to give 12.2 parts of a dioxazine compound (a compound of the formula (1) wherein R is ethyl and $Z^1$ and $Z^2$ are chlorine atom).

Example 15

10 parts of 3-amino-9-ethylcarbazole, 7 parts of chloranil, 4 parts of sodium carbonate, 2 parts of a compound of the formula (18) (a compound of the formula (3) wherein R' is ethyl, $Z^3$ and $Z^4$ are chlorine atom, X is phthalimidomethyl group, i is 2 and j is 0) and 100 parts of o-dichlorobenzene were mixed and stirred at 30°–65° C. for a reaction. On completion of condensation reaction, the reaction mixture was heated to 140°–150° C. under a reduced pressure, followed by adding 7 parts of p-toluenesulfonyl chloride at the same temperature and stirring at 165°–175° C. for 5 hours for a reaction. On completion of the reaction, the reaction product was cooled and produced crystals were filtered, washed with o-dichlorobenzene, methanol and water in that order and dried to give 12.3 parts of a dioxazine compound (a compound of the formula (1) wherein R is ethyl, and $Z^1$ and $Z^2$ are chlorine atom).

Example 16

To a mixture of 20 parts of 2,5-dichloro-3,6-bis(9-ethyl-3-carbazolylamino)-1,4-benzoquinone and 120 parts of o-dichlorobenzene was added an aqueous solution of a mixture of 0.2 part of a compound of the formula (7) and 0.8 part of a compound of the formula (19) (a compound of the formula (3) wherein R' is ethyl, $Z^3$ and $Z^4$ are chlorine atom, X is $CH_2NHCOCH_2$-Py lactate, i is 4 and j is 0), and the mixture was heated to 140°–150° C. under a reduced pressure, followed by adding 7 parts of p-toluenesulfonylchloride at the same temperature and stirring at 165°–175° C. for 5 hours for a reaction. On completion of the reaction, the reaction product was cooled and produced crystals were filtered, washed with o-dichlorobenzene, methanol and water in that order and dried to give 17.0 parts of a dioxazine compound (a compound of the formula (1) wherein R is ethyl, and $Z^1$ and $Z^2$ are chlorine atom).

Comparative Example 1

20 parts of 2,5-dichloro-3,6-bis(9-ethyl-3-carbazolylamino)-1,4-benzoquinone and 120 parts of o-dichlorobenzene were mixed and heated to 140°–150° C. under a reduced pressure. Then 8 parts of p-toluenesulfonyl chloride was added at the same temperature and the mixture was stirred at 165°–175° C. for 5 hours for a reaction. On completion of the reaction, the reaction product was cooled and produced crystals were filtered, washed with o-dichlorobenzene, methanol and water in that order and dried to give 16.7 parts of needle crystals of a dioxazine compound (a compound of the formula (1) wherein R is ethyl and $Z^1$ and $Z^2$ are chlorine atom).

Example 17

To 22 parts of the dioxazine compound obtained in Example 1, 33 parts of ethylene glycol and 150 parts of pulverized common salt were added and the mixture was kneaded for 7 hours to prepare a dispersed pigment. The ink produced by mixing this pigment with an ink varnish and shaking the mixture by a paint shaker had excellent gloss and color strength. In a coating test of this pigment using an alkyd resin, there was observed reddish tinting due to good dispersibility, the coloring power was high and the developed color was clear.

Examples 18 and 19

The procedure of Example 17 was repeated except that the dioxazine compounds obtained in Examples 8 and 9 were used in place of the dioxazine compound obtained in Example 1 to prepare dispersed pigments.

Comparative Example 2

The procedure of Example 17 was repeated except that the dioxazine compound obtained in Comparative Example 1 was used in place of the dioxazine compound obtained in Example 1 to prepare a dispersed pigment.

Comparative Example 3

The procedure of Example 17 was repeated except that 21 parts of the dioxazine compound obtained in Comparative Example 1 and 1 part of the compound of the formula (7) were used in place of 22 parts of the dioxazine compound obtained in Example 1 to prepare a dispersed pigment.

Deep-colored enamel paints were prepared from the above dispersed pigments using an alkyd resin varnish. There were also prepared light-colored enamels by mixing deed-colored enamels with a titanium dioxide paint. Obtained enamels were compared regarding color hue, color strength and gloss. The results are shown in Table 1.

TABLE 1

|  | Dioxazine compound used | Hue | Color Strength | Gloss |
|---|---|---|---|---|
| Example 17 | Example 1 | Reddish | 110 | Good |
| Example 18 | Example 8 | Reddish | 120 | Good |
| Example 19 | Example 9 | Reddish | 115 | Very good |
| Comp. Example 2 | Comp. Example 1 | Standard | Standard (100) | Standard |
| Comp. Example 3 | Comp. Example 1 + compound 7 | Bluish | 95 | Equal to standard |

Each of the light-colored enamels was applied on art paper, and hue and color strength of the enamel coating were visually judged with the sample of Comparative Example 2 as reference. The color-strength was judged by comparison of the color-strength of ink containing a pre-determined amount of sample with that of standard samples containing respective content. Gloss was visually judged from deep-colored enamel coating on art paper.

According to the present invention, a high-quality pigment crude can be obtained easily, and the pigment prepared therefrom shows excellent fastness properties such as light resistance, heat resistance, migration resistance, etc., when used for tinting of paints, resins, etc., or for pigment printing. Such a pigment also has excellent fluidity and gloss as well as high coloring value.

The present invention also provides a process for producing a dioxazine compound represented by the formula (1):

(wherein R represents a hydrogen atom or an alkyl group having 1–8 carbon atoms, and each of $Z^1$ and $Z^2$ independently represents a hydrogen atom or a halogen atom), which comprises reacting chloranil and a compound represented by the formula (5):

(wherein R is as defined above) in the presence of a compound represented by the formula (3):

(wherein R' represents a hydrogen atom or an alkyl group having 1–8 carbon atoms, each of $Z^3$ and $Z^4$ independently represents a hydrogen atom or a halogen atom, each of X and Y independently represents a substituent, i is a number of 0 to 6, and j is a number of 0 to 6, but i+j=1 to 6) to produce a compound represented by the formula (2):

(wherein R, $Z^1$ and $Z^2$ are as defined above), and subjecting this compound of the formula (2) to ring closure.

What is claimed is:

1. A process for producing a dioxazine compound represented by the formula (1):

wherein R represents a hydrogen atom or an alkyl group having 1 to 8 carbon atoms; and each of $Z^1$ and $Z^2$ independently represents a hydrogen atom or a halogen atom, which comprises subjecting a compound represented by the formula (2):

(2)

wherein R, $Z^1$ and $Z^2$ are as defined above, to ring closure reaction in the presence of a compound represented by the formula (3):

(3)

wherein R' represents a hydrogen atom or an alkyl group having 1 to 8 carbon atoms; each of $Z^3$ and $Z^4$ independently represents a hydrogen atom or a halogen atom; each of X and Y independently represents a substituent; i is a number of 1 to 6; and j is a number of 0 to 6, but i+j=1 to 6; said substituent represented by X is —A—$(CH_2)_l$—B or a phthalimidoalkyl group and said substituent represented by Y is —A'—$(CH_2)_n$—B' or a phthalimidoalkyl group (wherein A represents a divalent bonding group selected from —$SO_2$—, —CO—, —S—, —$CH_2NHCO$—, —O—, —$CONR^3$—, —$SO_2NR^4$— and $NR^5$ (wherein each of $R^1$, $R^2$, $R^3$, $R^4$ and $R^5$ independently represents a hydrogen atom or a saturated or unsaturated aliphatic or aromatic group which may contain a chalcogen atom, a nitrogen atom and/or a halogen atom); A' represents a divalent bonding group selected from —$SO_2$—, —CO—, —S—, —$CH_2NHCO$—, —O—, $CR^1R^2$—, —$CONR^3$—, —$SO_2NR^4$—and $NR^5$ (wherein each of $R^1$, $R^2$, $R^3$, $R^4$ and $R^5$ independently represents a hydrogen atom or a saturated or unsaturated aliphatic or aromatic group which may contain a chalcogen atom, a nitrogen atom and/or a halogen atom); each of B and B' independently represents a bonding group selected from —$OR^6$ (wherein $R^6$ represents a hydrogen atom, a metal atom or a saturated or unsaturated aliphatic or aromatic group which may contain a chalcogen atom, a nitrogen atom and/or a halogen atom), —$NR^7R^8$ and —$R^9$ (wherein each of $R^7$, $R^8$ and $R^9$ independently represents a hydrogen atom or a saturated or unsaturated aliphatic or aromatic group which may contain a chalcogen atom, a nitrogen atom and/or a halogen atom); and each of n and l independently represents a number of 0 to 8)).

2. The process according to claim 1, wherein A is —$SO_2$— or —$SO_2NR^4$—; l is a number of 0 to 8; B is —$OR^6$, —$NR^7R^8$ or —$R^9$; A' is —$SO_2$—; n is 0, B' is —$OR^6$; i is a number of 1 to 6; and j is a number of 0 to 5.

3. The process according to claim 1, wherein A is —O—, $CR^1R^2$—, $CH_2NHCO$— or —$CONR^3$—; l is an integer of 0 to 8; B is a bonding group selected from —$OR^6$, —$NR^7R^8$ or —$R^9$; i is an integer of 1 to 6; and j is 0.

4. The process according to claim 1, wherein the compound of the formula (3) is a compound in which —$SO_3M$ (M being a hydrogen atom or a metal atom) is bonded to the compound of the formula (1); a compound in which an alkylaminosulfonyl group, an alkylaminoalkylaminosulfonyl group or a group represented by the formula —$SO_2N(R_{11})_2$ (wherein $R_{11}$ is $(CH_2CH_2O)_nH$ (n being a number of 1 to 30)) are bonded to the compound of the formula (1); a compound in which an alkoxy group having 1-8 carbon atoms is bonded to the compound of the formula (1); a compound in which a phthalimidoalkyl group, an alkylcarbonylaminoalkyl group or an alkylaminoalkylcarbonylaminoalkyl group are bonded to the compound of the formula (1); or a compound in which an alkylaminocarbonyl group or an alkylaminoalkylaminocarbonyl group are bonded to the compound of the formula (1).

5. The process according to claim 1, wherein the compound of the formula (3) is a compound in which 1 to 6 sulfonic acid groups are bonded to the compound of the formula (1), a part or whole thereof being salts.

6. The process according to claim 1, wherein the compound of the formula (3) is a compound in which 1 to 5 alkylaminosulfonyl groups, alkylaminoalkylaminosulfonyl groups or groups of the formula —$SO_2N(R_{11})_2$ (wherein $R_{11}$ is $(CH_2CH_2O)_nH$ (n being a number of 1 to 30)) and 0 to 3 sulfonic groups or salts thereof (the total number of substituents being 1 to 6) are bonded as substituents to the compound of the formula (1).

7. The process according to claim 1, wherein the compound of the formula (3) is a compound in which 1 to 5 pyridiniumalkylcarbonylaminoalkyl group or trialkylammoniumalkylcarbonylaminoalkyl group and 0 to 3 sulfonic acid groups or salts thereof (the total number of substituents being 1 to 6) are bonded as substituents to the compound of the formula (1) and the pair ion is chloride ion, lactic acid ion, acetic acid ion or methylsulfuric acid ion.

8. The process according to claim 5, 6 or 7, wherein the salt is an alkaline metal salt.

9. The process according to claim 1, wherein the amount of the compound of the formula (3) used falls within the range of from 0.005 to 0.3 part by weight per 1 part by weight of the compound of the formula (2).

10. The process according to claim 1, 4, 5, 6 or 9, wherein the ring closure reaction is carried out under heating at a temperature of from 100° to 200° C. in the presence of the compound of the formula (3) in an amount of 0.005 to 0.3 part by weight per 1 part by weight of the compound of the formula (2) and a ring-closing agent.

11. The process according to claim 10, wherein the amount of the ring-closing agent used falls within the range of from 0.1 to 5 moles per 1 mole of the compound of the formula (2).

* * * * *